United States Patent
Inada

(10) Patent No.: US 10,401,612 B2
(45) Date of Patent: Sep. 3, 2019

(54) ENDOSCOPE

(71) Applicant: OLYMPUS CORPORATION, Tokyo (JP)

(72) Inventor: Ayumu Inada, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 710 days.

(21) Appl. No.: 14/953,941

(22) Filed: Nov. 30, 2015

(65) Prior Publication Data

US 2016/0077323 A1 Mar. 17, 2016

Related U.S. Application Data

(63) Continuation of application No. PCT/JP2014/062087, filed on May 1, 2014.

(30) Foreign Application Priority Data

May 31, 2013 (JP) ................. 2013-115370

(51) Int. Cl.
  *A61B 1/00* (2006.01)
  *G02B 23/24* (2006.01)
  (Continued)

(52) U.S. Cl.
  CPC ...... *G02B 23/2476* (2013.01); *A61B 1/00096* (2013.01); *A61B 1/00101* (2013.01);
  (Continued)

(58) Field of Classification Search
  CPC .............. A61B 1/00059; A61B 1/0008; A61B 1/00101; G02B 23/2476
  (Continued)

(56) References Cited

U.S. PATENT DOCUMENTS 6,095,970 A * 8/2000 Hidaka ............... A61B 1/00124
  600/109
6,184,923 B1 * 2/2001 Miyazaki ........... A61B 1/00096
  348/75
(Continued)

FOREIGN PATENT DOCUMENTS

JP  2000-047121 A  2/2000
JP  2004-313241 A  11/2004
(Continued)

OTHER PUBLICATIONS

International Search Report dated Jul. 15, 2014 received from International Application No. PCT/JP2014/062087.

(Continued)

*Primary Examiner* — Matthew J Kasztejna
(74) *Attorney, Agent, or Firm* — Scully, Scott, Murphy & Presser, P.C.

(57) ABSTRACT

An endoscope includes a mounting and detaching section, terminals that, when an adapter is mounted on an outer circumference, come into contact with an identification resistor provided in the adapter and having different resistance values for each of adapters, a lead wire that energizes the identification resistor via the terminals, and a flexible board electrically connected to the terminals in the mounting and detaching section and electrically connected to a distal end of the lead wire in a position behind the mounting and detaching section.

13 Claims, 11 Drawing Sheets

(51) Int. Cl.
*G02B 7/14* (2006.01)
*G02B 23/26* (2006.01)

(52) U.S. Cl.
CPC ...... *A61B 1/00105* (2013.01); *A61B 1/00114* (2013.01); *A61B 1/00124* (2013.01); *G02B 7/14* (2013.01); *G02B 23/243* (2013.01); *G02B 23/26* (2013.01); *A61B 1/00059* (2013.01)

(58) Field of Classification Search
USPC .................................................. 600/127, 129
See application file for complete search history.

(56) References Cited

U.S. PATENT DOCUMENTS

| | | | |
|---|---|---|---|
| 2005/0014996 A1* | 1/2005 | Konomura | G02B 23/2407 600/175 |
| 2005/0177027 A1* | 8/2005 | Hirata | A61B 1/0676 600/179 |
| 2005/0240077 A1* | 10/2005 | Rovegno | G02B 23/2423 600/108 |
| 2007/0106119 A1 | 5/2007 | Hirata et al. | |
| 2010/0188493 A1 | 7/2010 | Kanzaki et al. | |

FOREIGN PATENT DOCUMENTS

| | | |
|---|---|---|
| JP | 2008-36034 A | 2/2008 |
| JP | 2009-446 A | 1/2009 |
| JP | 2009-11511 A | 1/2009 |
| JP | 2011-10949 A | 1/2011 |
| JP | 2011-24954 A | 2/2011 |
| JP | 2011-170094 A | 9/2011 |

OTHER PUBLICATIONS

Extended Supplementary European Search Report dated Jan. 16, 2017 in related European Patent Application No. 14 80 3409.3.

* cited by examiner

ENDOSCOPE

CROSS REFERENCE TO RELATED APPLICATION

This application is a continuation application of PCT/JP2014/062087 filed on May 1, 2014 and claims benefit of Japanese Application No. 2013-115370 filed in Japan on May 31, 2013, the entire contents of which are incorporated herein by this reference.

BACKGROUND OF THE INVENTION

1. Field of the Invention

The present invention relates to an endoscope in which two or more kinds of adapters are individually detachably attachable to a distal end portion located at a distal end in an inserting direction of an insertion section.

2. Description of the Related Art

As is well known, endoscopes are widely used in a medical field and an industrial field. With an endoscope used in the medical field, it is possible to, by inserting an elongated insertion section into a body cavity serving as a subject, observe an organ in the body cavity and perform various kinds of treatment using a treatment instrument inserted into a treatment instrument insert-through channel according to necessity.

With an endoscope used in the industrial field, it is possible to, by inserting an elongated insertion section into a jet engine, a pipe in a factory, or the like serving as an object, perform observation, various kinds of treatment, and the like of scratches, corrosion, and the like in the object.

A configuration is well known in which, in a distal end portion located on a distal end side in an inserting direction of an insertion section of an endoscope (hereinafter simply referred to as distal end side), an image pickup unit including an objective lens unit and an image pickup device such as a CCD is provided and an illumination unit or the like that illuminates an inside of an object is provided.

A configuration is also well known in which the objective lens unit and the illumination unit are provided in a known optical adapter (hereinafter simply referred to as adapter) detachably attachable to the distal end portion of the insertion section.

As the adapter, a direct-view adapter for observing a front in the inserting direction of the insertion section (hereinafter simply referred to as front) and a side-view adapter for observing a side different from the inserting direction are well known. The respective adapters are properly used according to observation targets and uses.

Further, a plurality of adapters having different visual field angles is present in each of the direct-view adapter and the side-view adapter. These adapters are also properly used according to observation targets and uses. Therefore, a plurality of kinds of adapters is individually detachably attachable to the distal end portion.

Japanese Patent Application Laid-Open Publication No. 2004-313241 discloses a configuration in which, in a plurality of adapters detachably attachable to a distal end portion, identification resistors having different resistance values for each of the adapters are provided and, when an adapter is attached to the distal end portion, an identification resistor comes into contact with a terminal for resistor identification provided in the distal end portion and energizes the identification resistor, whereby a CPU electrically connected to the terminal via a lead wire in a control unit, to which an endoscope is connected, reads a resistance value and automatically detects a type of the adapter attached to the distal end portion from the resistance value.

Japanese Patent Application Laid-Open Publication No. 2004-313241 also discloses a configuration in which, since it is difficult to reduce the adapter or the distal end portion in diameter if a light source such as a light emitting element is provided in the adapter or the distal end portion of an insertion section, the light source is provided in the control unit, a light guide that guides illumination light irradiated from the light source to a distal end face located at a distal end in an inserting direction of the distal end portion (hereinafter simply referred to as distal end) is inserted through the endoscope, the illumination light emitted from a distal end of the light guide is made incident in the adapter, and an illumination optical system that supplies the illumination light into an object is provided.

Incidentally, in general, the attachment of the adapter to the distal end portion including the configurations disclosed in Japanese Patent Application Laid-Open Publication No. 2004-313241 is performed by coating, with an inner circumference of a proximal end side in the inserting direction of the adapter (hereinafter simply referred to as proximal end side), an outer circumference of a mounting and detaching section located on a distal end side of the distal end portion and screwing, for example, with a male screw formed in the outer circumference of the mounting and detaching section, a female screw formed in an inner circumference of a stop ring extending from a proximal end in the inserting direction of the adapter (hereinafter simply referred to as proximal end) backward in the inserting direction (hereinafter simply referred to as backward).

In the distal end portion including the mounting and detaching section, built-in components such as the lens unit in the image pickup unit, the terminal functioning as a member for adapter identification explained above, the lead wire extending from the terminal, the light guide explained above, and various channels are provided.

SUMMARY OF THE INVENTION

An endoscope according to an aspect of the present invention is an endoscope in which two or more kinds of adapters are individually detachably attachable to a distal end portion located at a distal end in an inserting direction of an insertion section. The endoscope includes: a mounting and detaching section located on the distal end side in the inserting direction in the distal end portion, a connecting section of the adapter being detachably mountable on an outer circumference of the mounting and detaching section and a diameter of the mounting and detaching section being smaller than a diameter of another part of the distal end portion; a terminal provided to be exposed on a distal end face of the distal end in the inserting direction in the distal end portion in the mounting and detaching section, when the adapter is mounted on the outer circumference of the mounting and detaching section, the terminal coming into contact with an identification resistor provided in the adapter and having different resistance values for each of the adapters; a lead wire inserted through the insertion section, the lead wire energizing the identification resistor via the terminal; and a flexible board inserted through at least the mounting and detaching section, the flexible board being electrically connected to the terminal in the mounting and detaching section and electrically connected to a distal end in the inserting direction of the lead wire in a position behind the mounting and detaching section in the inserting direction.

DETAILED DESCRIPTION OF THE PREFERRED EMBODIMENTS

Embodiments of the present invention are explained below with reference to the drawings. Note that, in the following explanation, as an endoscope, an endoscope for industrial use is explained as an example.
(First Embodiment)

Figure 1:
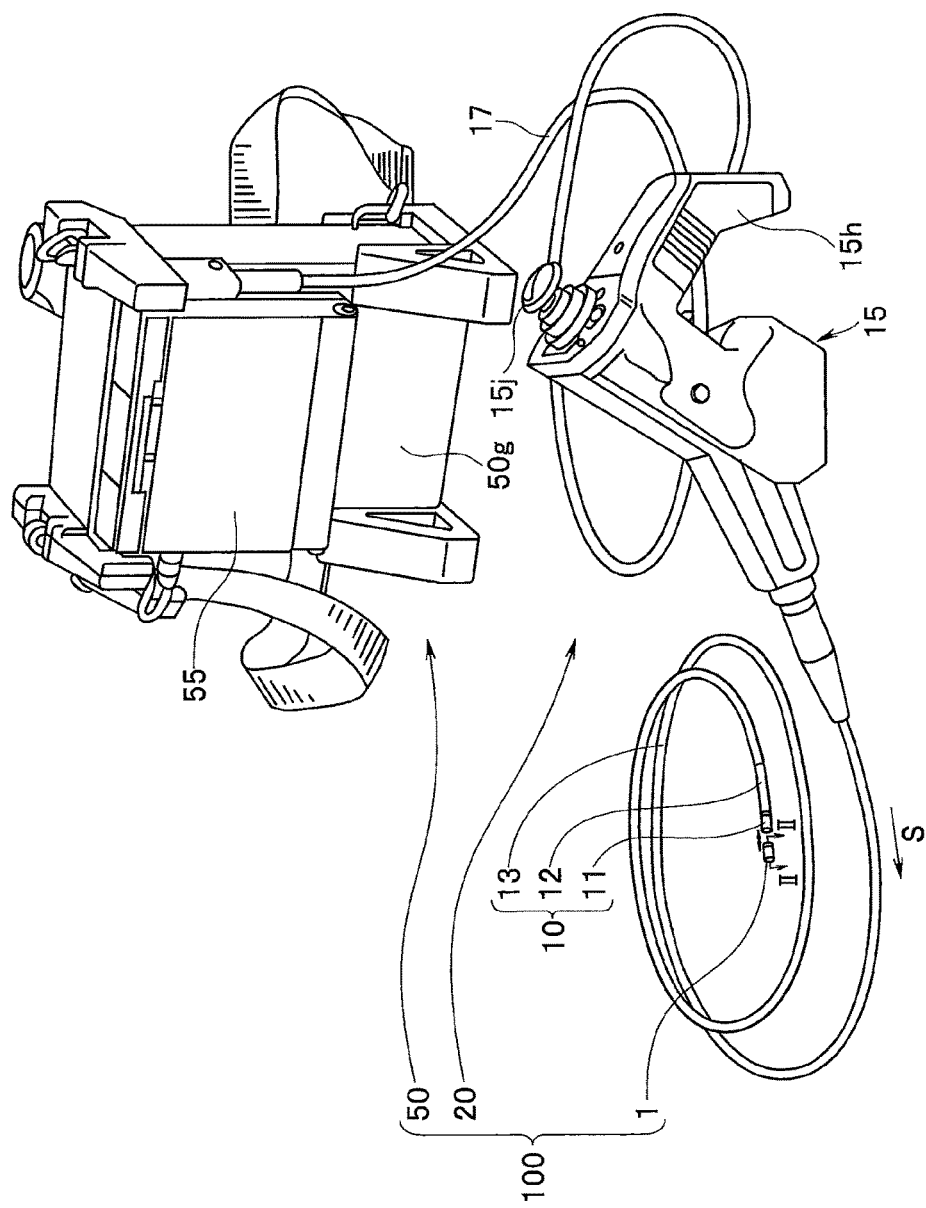
FIG. 1 is a perspective view of an endoscope system including an endoscope showing a first embodiment.

FIG. 1 is a perspective view of an endoscope system including an endoscope showing the present embodiment.

As shown in FIG. 1, in an endoscope system 100, a main part is configured by an endoscope 20, an apparatus main body 50 connected to the endoscope 20, and two or more kinds of adapters 1. Note that, in the following explanation, in order to simplify the drawings and explanation, description of the adapter 1 is common to all of the two or more kinds of adapters.

In the endoscope 20, a main part is configured by including an elongated and flexible insertion section 10, an operation section 15 connected to a proximal end in an inserting direction S of the insertion section 10 and including a grasping section 15h, and a universal cord 17 extended from the grasping section 15h of the operation section 15.

A distal end portion 11 to which the two or more kinds of adapters 1 are individually detachably attachable, a bending section 12 bendable in, for example, upward, downward, left, and right four directions according to operation of a joystick 15j provided in the operation section 15, and a long flexible tube section 13 formed of a flexible member are concatenated to the insertion section 10 in order from a distal end side of the insertion section 10. A proximal end of the flexible tube section 13 is connected to the operation section 15.

Note that, in the operation section 15, besides the joystick 15j, for example, various not-shown switches for instructing an image pickup operation in an image pickup device 27 (see FIG. 4) explained below provided in the distal end portion 11 are provided.

The apparatus main body 50 has, for example, a box shape. A monitor 55 that displays an endoscopic image picked up by an image pickup device 27 (see FIG. 4) of the endoscope 20 is fixed to an armor housing 50g, which is configured by, for example, magnesium die cast, to be capable of opening and closing with respect to, for example, the armor housing 50g. Note that the monitor 55 may be detachably attachable to the armor housing 50g or may be fixed to the armor housing 50g in a state in which a monitor surface is always exposed.

Next, a configuration of the adapter and a configuration of the distal end portion are explained with reference to FIG. 2 to FIG. 9.

Figure 2:
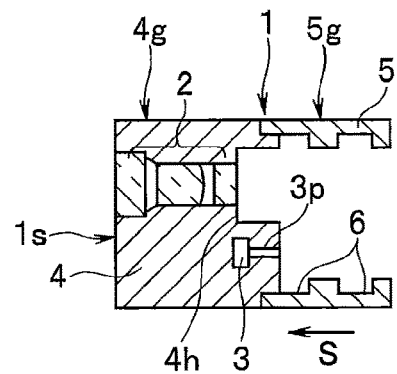
FIG. 2 is a sectional view of an adapter shown in FIG. 1 taken along line II-II.
Figure 3:
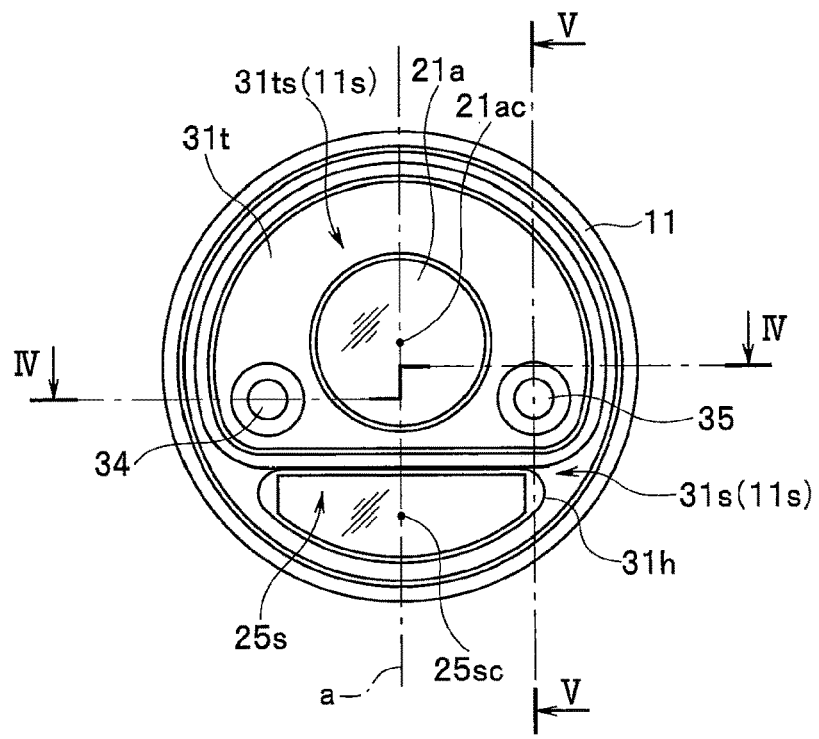
FIG. 3 is a plan view showing a distal end face of a distal end portion in FIG. 1.
Figure 4:
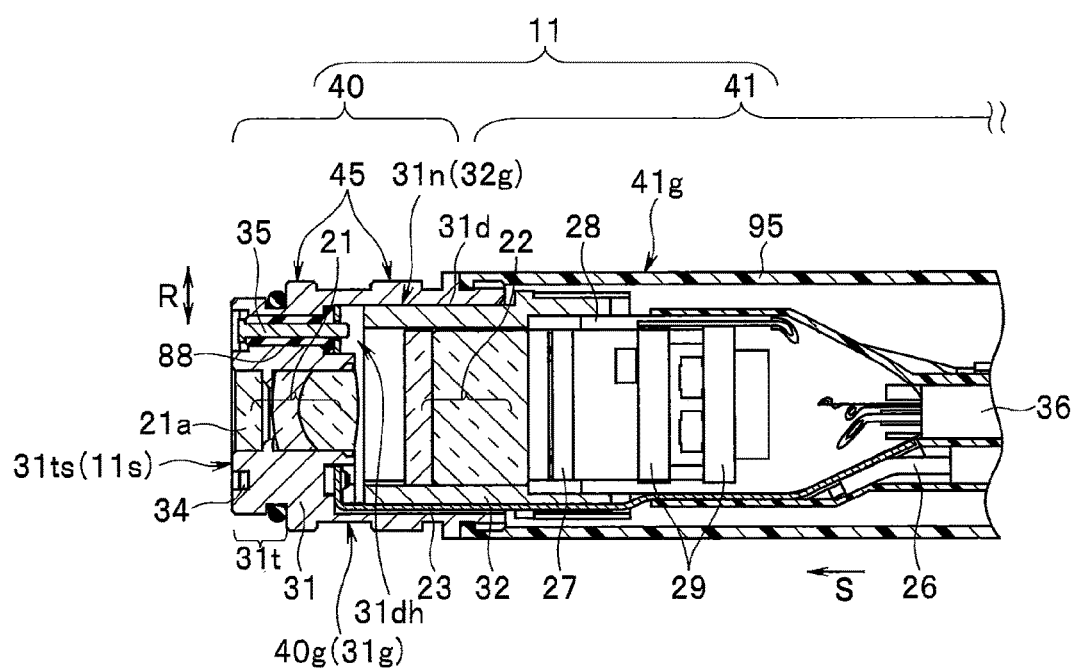
FIG. 4 is a sectional view of a distal end portion taken along line IV-IV in FIG. 3.
Figure 5:
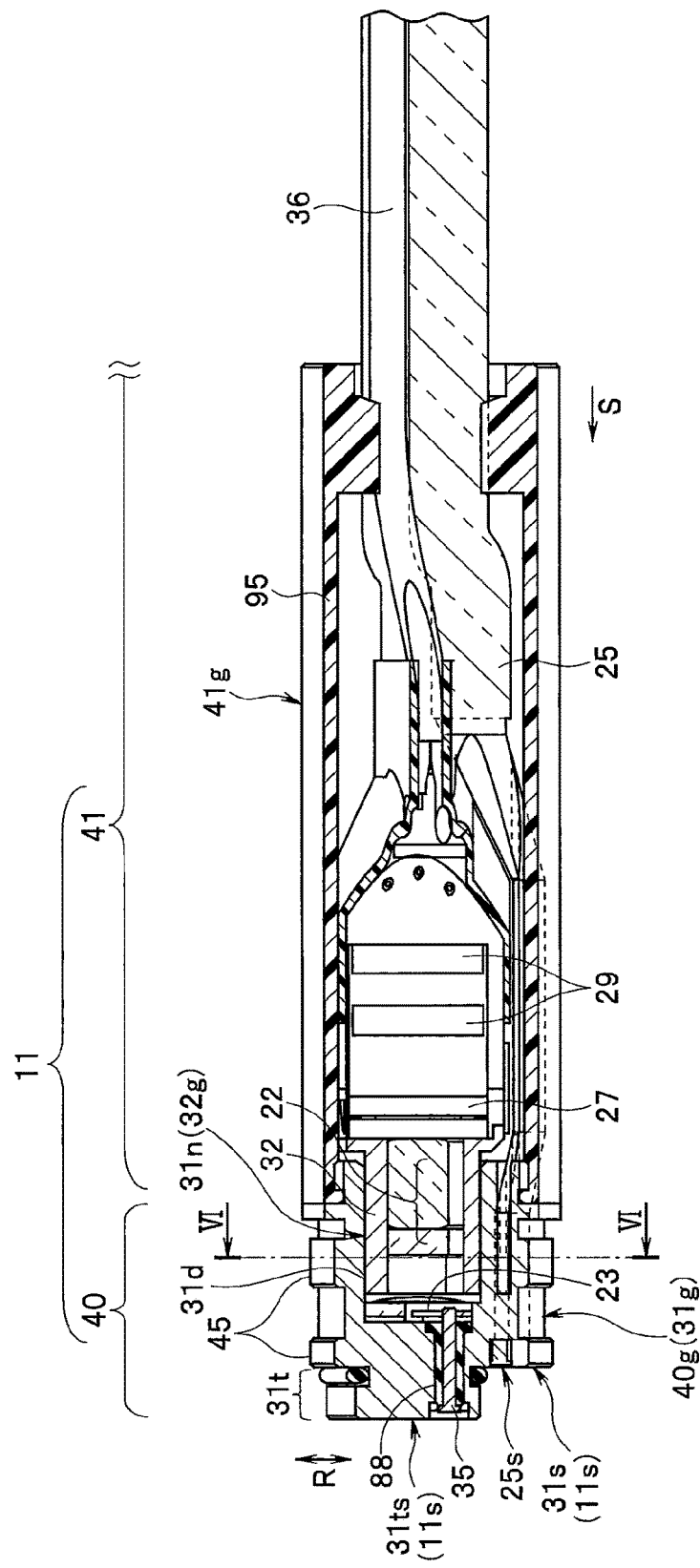
FIG. 5 is a sectional view of the distal end portion taken along line V-V in FIG. 3.

FIG. 2 is a sectional view of the adapter in FIG. 1 taken along line II-II. FIG. 3 is a plan view showing a distal end face of the distal end portion in FIG. 1. FIG. 4 is a sectional view of the distal end portion taken along line IV-IV in FIG. 3. FIG. 5 is a sectional view of the distal end portion taken along line V-V in FIG. 3.

Figure 6:
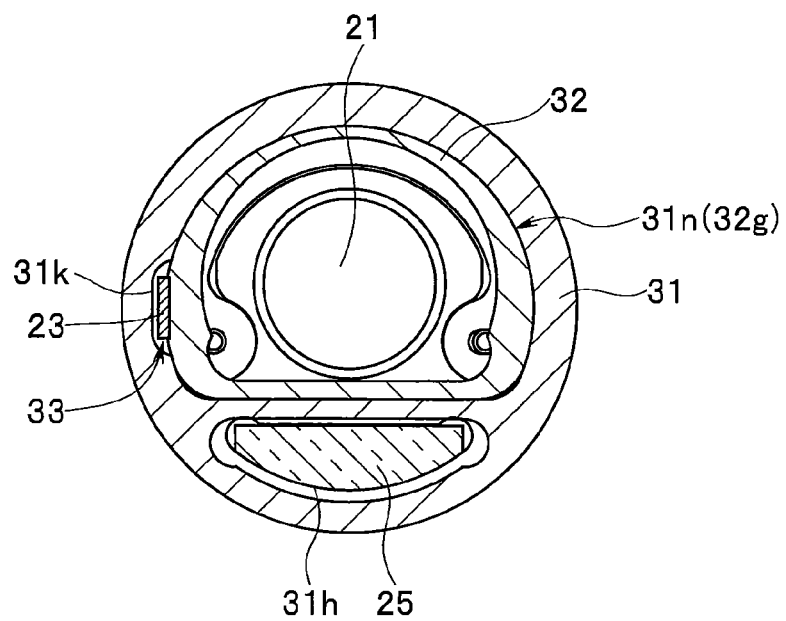
FIG. 6 is a sectional view of the distal end portion taken along line VI-VI in FIG. 5.
Figure 7:
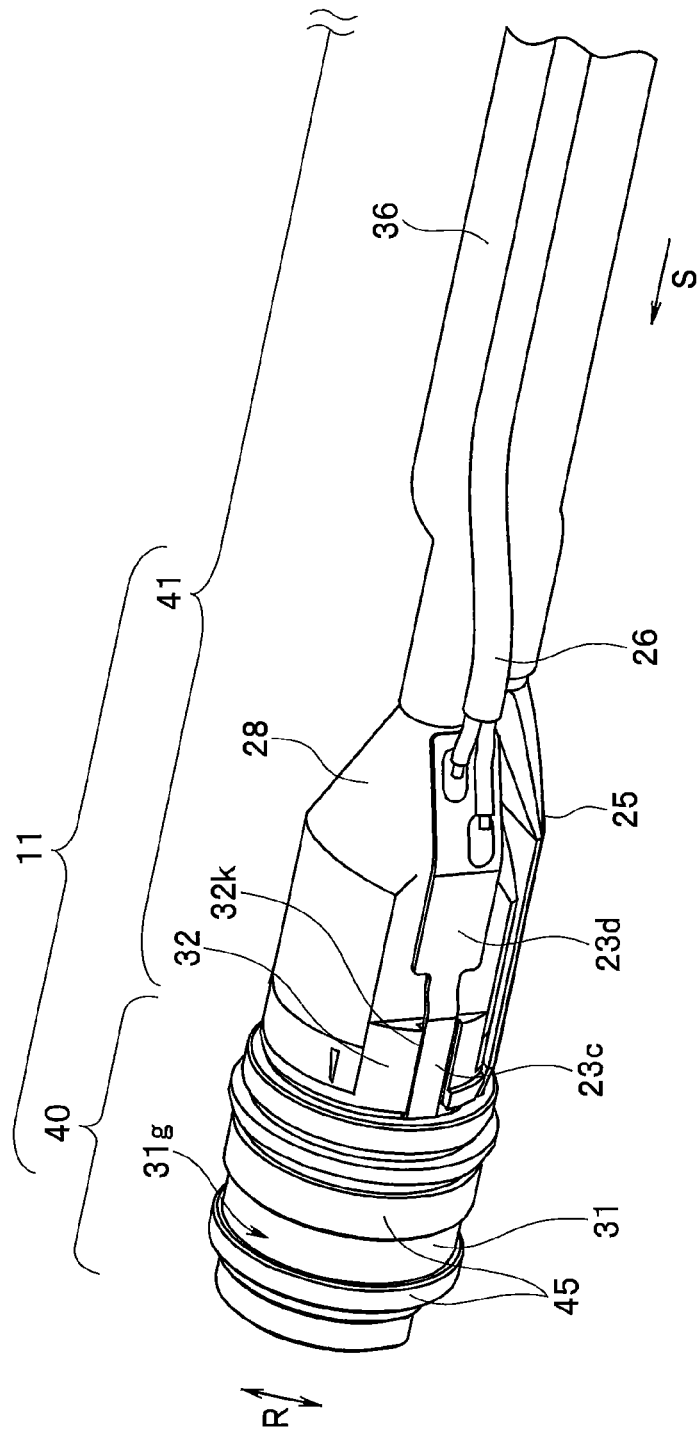
FIG. 7 is a perspective view showing the distal end portion in FIG. 4 and FIG. 5 excluding an image pickup cover.
Figure 8:
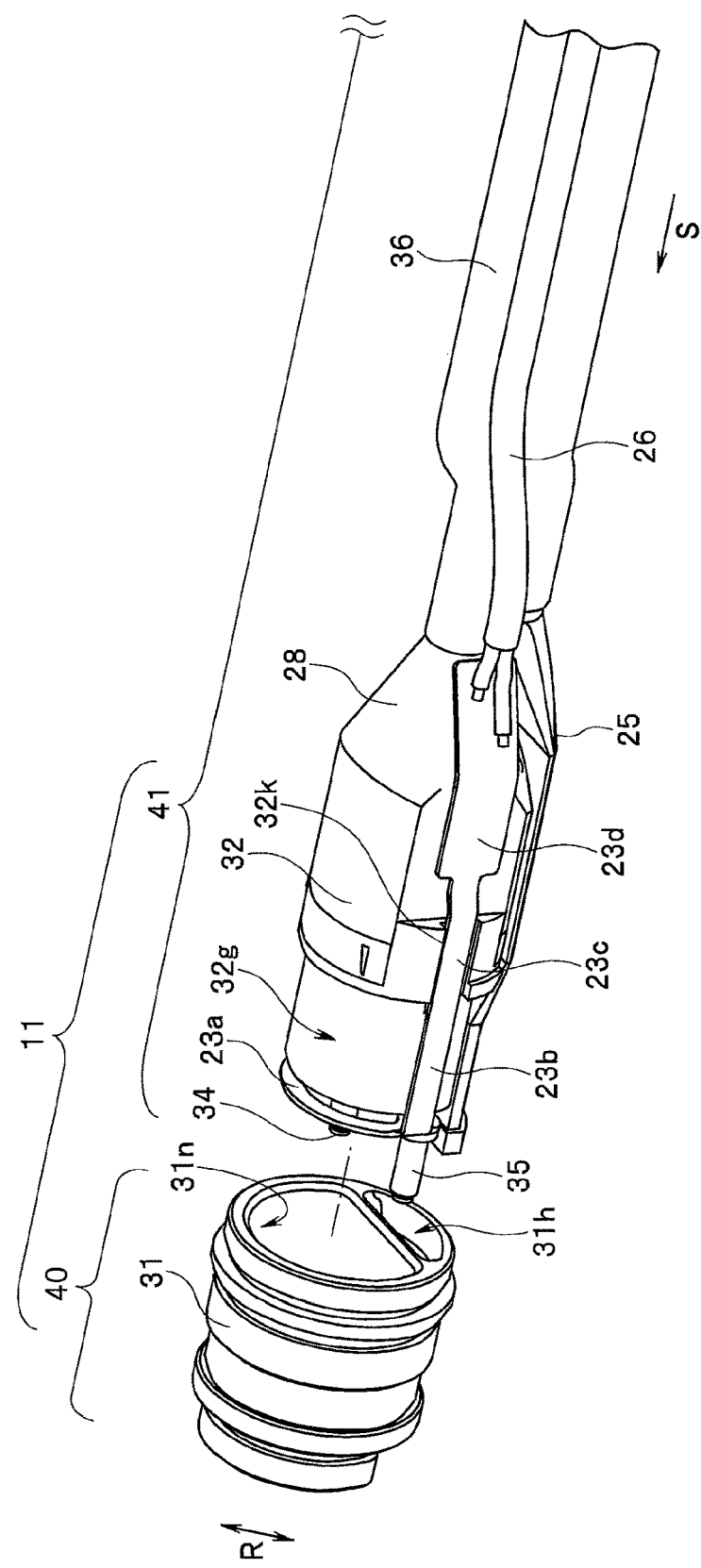
FIG. 8 is an exploded perspective view in which a distal end portion main body is separated at the distal end portion in FIG. 7.
Figure 9:
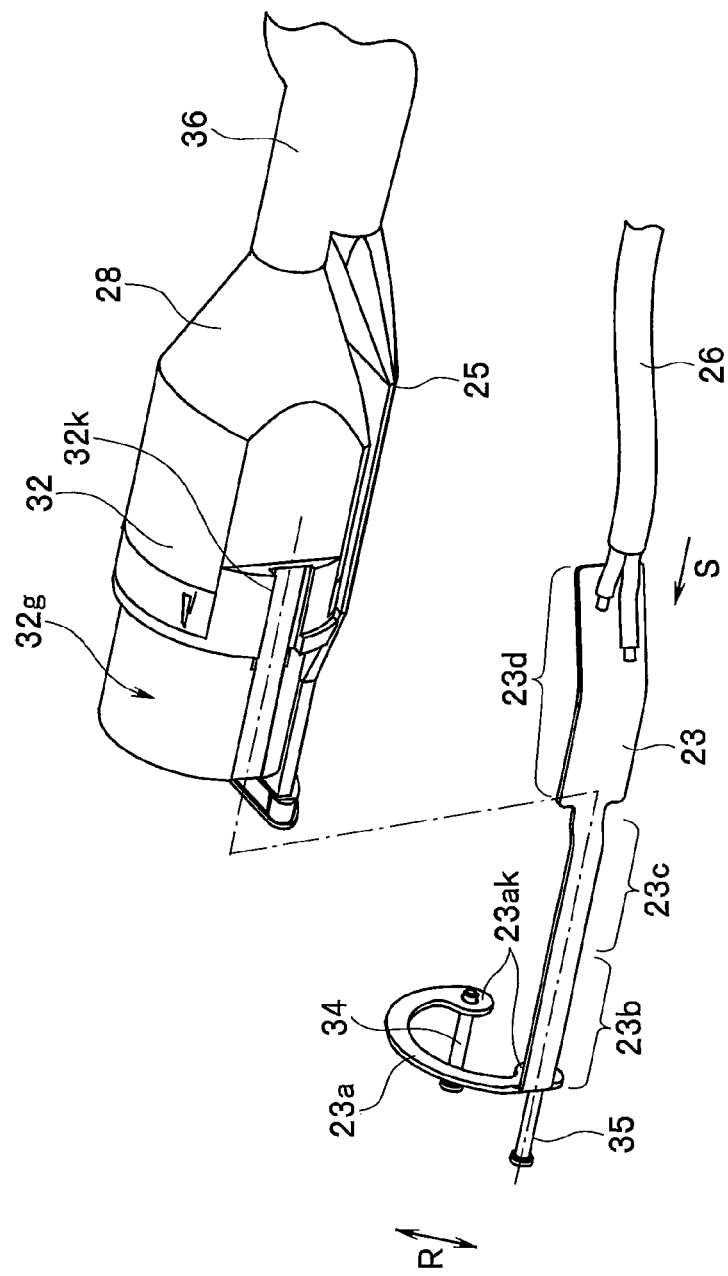
FIG. 9 is an exploded perspective view in which a flexible board is separated from a part other than a mounting and detaching section at the distal end portion in FIG. 8.

FIG. 6 is a sectional view of the distal end portion taken along line VI-VI in FIG. 5. FIG. 7 is a perspective view showing the distal end portion in FIG. 4 and FIG. 5 excluding an image pickup cover. FIG. 8 is an exploded perspective view in which a distal end portion main body is separated at the distal end portion in FIG. 7. FIG. 9 is an exploded perspective view in which a flexible board is separated from a part other than a mounting and detaching section at the distal end portion in FIG. 8.

As shown in FIG. 4 and FIG. 5, the distal end portion 11 includes a mounting and detaching section 40 located on a distal end side in the distal end portion 11. The adapter 1 is detachably mountable on an outer circumference 40g of the mounting and detaching section 40. The mounting and detaching section 40 is smaller in diameter than the other part 41 of the distal end portion 11.

The mounting and detaching section 40 includes, on an inside, a distal end portion main body 31, which is a first frame, formed in a substantially columnar shape. Note that an outer circumference 31g of the distal end portion main body 31 configures the outer circumference 40g of the mounting and detaching section 40. In the outer circumference 31g of the distal end portion main body 31, a male screw 45 is formed, with which a female screw 6 of a stop ring 5 (for both of which, see FIG. 2) explained below of the adapter 1 is capable of being fit when the adapter 1 is mounted on the mounting and detaching section 40.

On a distal end face 31s of the distal end portion main body 31, a projecting section 31t projecting forward from the distal end face 31s is formed. Note that the distal end face 31s configures a distal end face 11s of the distal end portion 11.

The projecting section 31t is a member for, when the adapter 1 is mounted on the mounting and detaching section 40, performing positioning of the adapter 1 with respect to the distal end portion 11 by being fit in a recessed section 4h formed on a proximal end face of an adapter main body 4 explained below of the adapter 1.

In the distal end portion main body 31 and the projecting section 31$t$, a lens unit 21, which is a first objective optical system, for observing an inside of an object is provided.

The lens unit 21 is configured from a plurality of lenses, for example, three lenses. As shown in FIG. 3 and FIG. 4, an objective lens 21$a$ located most forward in the inserting direction S is fixed to the distal end portion main body 31 to be exposed on a distal end face 31$ts$ of the projecting section 31$t$. Note that the number of the lenses configuring the lens unit 21 is not limited to three. The distal end face 31$ts$ configures the distal end face 11$s$ of the distal end portion 11.

As shown in FIG. 3, in the distal end portion main body 31, a light guide holding hole 31$h$ piercing through the distal end portion main body 31 along the inserting direction S is formed in a position in the figure lower than the objective lens 21$a$ as shown in FIG. 3. The universal cord 17 of the endoscope 20, and a distal end side of a light guide 25 inserted through the operation section and the insertion section 10 are inserted through the light guide holding hole 31$h$. As shown in FIG. 3 and FIG. 5, an emission end face 25$s$ is fixed to be exposed on the distal end face 31$s$.

Note that a proximal end of the light guide 25 is located to be opposed to a not-shown light source provided in the apparatus main body 50. As shown in FIG. 5 and FIG. 7 to FIG. 9, in the other part 41 at the distal end portion 11, the light guide 25 is inserted through to extend along outer circumferences of a lens frame 32 and a device frame 28 explained below in a position in the figure lower than the lens frame 32, the image pickup device 27, an electric circuit boards 29, and a signal line 36 explained below.

The light guide 25 guides illumination light made incident from the proximal end to the emission end face 25$s$ of the light guide 25 and, when the adapter 1 is mounted on the mounting and detaching section 40, supplies the illumination light irradiated from the emission end face 25$s$ to the adapter 1. Note that the illumination light supplied to the adapter 1 is irradiated on the inside of the object via a not-shown illumination optical system provided in the adapter 1.

As shown in FIG. 3 to FIG. 5, in the distal end portion main body 31 and the projecting section 31$t$, two terminals 34 and 35 that come into contact with pins 3$p$ of an identification resistor 3 (for both of which, see FIG. 2) explained below, which is provided in the adapter 1 and have different resistance values for each adapter 1, when the adapter 1 is mounted on the mounting and detaching section 40 are provided such that distal ends of the terminals 34 and 35 are exposed on the distal end face 31$ts$ of the projecting section 31$t$. Note that, as shown in FIG. 4 and FIG. 5, insulating members 88 are respectively coated on outer circumferences of the terminals 34 and 35.

The terminal 34 configures an anode terminal electrically connected to, via the pin 3$p$, an anode side of the identification resistor 3 provided in the adapter 1 when the adapter 1 is mounted on the mounting and detaching section 40. The terminal 35 configures a cathode terminal electrically connected to, via the pin 3$p$, a cathode side of the identification resistor 3 provided in the adapter 1 when the adapter 1 is mounted on the mounting and detaching section 40.

As shown in FIG. 3, the terminals 34 and 35 are provided to be separated from each other on the distal end face 31$ts$ in positions where the terminals 34 and 35 sandwich the objective lens 21$a$ in plan view of the distal end face 31$ts$.

More specifically, as shown in FIG. 3, the terminals 34 and 35 are provided to be separated from each other such that distal ends thereof are exposed in positions on the distal end face 31$ts$ line-symmetrical with respect to a line "a" that connects a center 21$ac$ of the objective lens 21$a$ and a center 25$sc$ of the emission end face 25$s$ of the light guide 25.

Note that, on the distal end face 31$ts$, a reason for providing the terminals 34 and 35 to be separated from each other in the positions where the terminals 34 and 35 sandwich the objective lens 21$a$ is to insert the terminals 34 and 35 through the projecting section 31$t$ such that the distal ends are exposed on the distal end face 31$ts$ without increasing an area of the distal end face 31$ts$, that is, without increasing the projecting section 31$t$ in diameter.

This is because, on the distal end face 31$ts$, for example, if it is attempted to provide the terminal 34 in a position right above the terminal 35 side by side, the area of the distal end face 31$ts$ has to be increased in order to secure a disposition region of the terminal 34 on the distal end face 31$ts$ and, as a result, the projecting section 31$t$ is increased in diameter but, if the terminals 34 and 35 are disposed to be separated from each other to sandwich the objective lens 21$a$ as shown in FIG. 3, since the terminals 34 and 35 can be disposed in a free region of the distal end face 31$ts$ even if the area of the distal end face 31$ts$ is not increased, it is possible to reduce the projecting section 31$t$, that is, the mounting and detaching section 40 in diameter.

Therefore, the disposition positions of the terminals 34 and 35 on the distal end face 31$ts$ are not limited to the positions shown in FIG. 3. The terminals 34 and 35 may be disposed in any positions other than a disposition region of the objective lens 21$a$ on the distal end face 31$ts$ as long as the mounting and detaching section 40 is not increased in diameter in the positions.

As shown in FIG. 2, the adapter 1 mounted on the outer circumference 40$g$ of the mounting and detaching section 40 includes the adapter main body 4 formed in a substantially columnar shape.

On a proximal end face of the adapter main body 4, the recessed section 4$h$ formed to be recessed forward from the proximal end face along the inserting direction S is formed in a position opposed to the projecting section 31$t$ when the adapter 1 is mounted on the mounting and detaching section 40.

The recessed section 4$h$ is a part in which the projecting section 31$t$ fits as explained above when the adapter 1 is mounted on the mounting and detaching section 40.

A stop ring 5, which is a connecting section, in an inner circumference of which the female screw 6 is formed, is extended backward from an outer circumference of a proximal end of the adapter main body 4. The stop ring 5 is screwed with the male screw 45 formed in the outer circumference 31$g$ of the distal end portion main body 31 when the adapter 1 is mounted on the mounting and detaching section 40, that is, the projecting section 31$t$ is fit in the recessed section 4$h$. Consequently, the adapter 1 is fixed to an outer circumference of the mounting and detaching section 40. Note that, since the female screw 6 is capable of being screwed with the male screw 45, the adapter 1 is detachably mountable on the mounting and detaching section 40.

Note that an outer diameter of an outer circumference 4$g$ of the adapter main body 4 and an outer diameter of an outer circumference 5$g$ of the stop ring 5 are formed substantially the same as an outer diameter of an outer circumference 41$g$ of the other part 41 of the distal end portion 11 when the adapter 1 is mounted on the mounting and detaching section 40. Consequently, even if the adapter 1 is mounted on the mounting and detaching section 40, an outer circumference of the adapter 1 is not located to protrude further to an outer side in a radial direction R than an outer circumference of the distal end portion 11.

In the adapter main body 4, in a position overlapping the recessed section 4h along the inserting direction S, an objective lens unit 2 for observing the inside of the object configured from a plurality of lenses, for example, three lenses is fixed such that a lens located most forward is exposed on a distal end face 1s of the adapter 1. Note that the number of lenses configuring the objective lens unit 2 is not limited to three.

Therefore, when the adapter 1 is mounted on the mounting and detaching section 40, an observation part in the object is subjected to image pickup by the image pickup device 27 via the objective lens unit 2 and lens units 21 and 22 (for all of which, see FIG. 4 and FIG. 5) explained below.

In the adapter main body 4, in a position opposed to the emission end face 25s of the light guide 25, an illumination optical system configured from a not-shown elongated rod lens and a not-shown illumination lens along the inserting direction S is fixed such that the illumination lens is exposed on the distal end face 1s when the adapter 1 is mounted on the mounting and detaching section 40.

In the adapter main body 4, the identification resistor 3, which has a different resistance value for each of a plurality of adapters 1, electrically connected to the terminals 34 and 35 when the adapter 1 is mounted on the mounting and detaching section 40 is provided.

On an anode side and a cathode side of the identification resistor 3, the pins 3p such as sliding pins movable back and forth in the inserting direction S are respectively electrically connected. On the proximal end face of the adapter main body 4, proximal ends of the respective pins 3p are exposed in positions where the terminals 34 and 35 come into contact with the pins 3p when the adapter 1 is mounted on the mounting and detaching section 40.

Referring back to FIG. 4 and FIG. 5, a recessed section 31d recessed forward is formed on a proximal end face of the distal end portion main body 31. An outer circumference of a part of a lens frame 32, which is a second frame, is fit and fixed to an inner circumference 31n formed by the recessed section 31d.

In the lens frame 32, in a position overlapping the lens unit 21 in the inserting direction S, a lens unit 22, which is a second objective optical system, configured from a plurality of lenses, for example, two lenses is fixed to be located behind the lens unit 21. Note that the number of lenses configuring the lens unit 22 is not limited to two.

An outer circumference on a distal end side of a device frame 28, on an inside of which the image pickup device 27 such as a CCD or a C-MOS and the electric circuit boards 29 are fixed, is fixed to an inner circumference on a proximal end side of the lens frame 32.

When the adapter 1 is mounted on the mounting and detaching section 40, the image pickup device 27 picks up an image of an observation part in the object via the objective lens unit 2 and the lens units 21 and 22.

Note that the electric circuit boards 29 for adjusting an electric output of the image pickup device 27 are electrically connected to the image pickup device 27. The universal cord 17, the operation section 15, and a distal end of a signal line 36 inserted through the insertion section 10 are electrically connected to the electric circuit boards 29.

A proximal end of the signal line 36 is connected to a not-shown image processing unit or the like in the apparatus main body 50. Consequently, the image of the observation part picked up by the image pickup device 27 is transmitted to the image processing unit in the apparatus main body 50 via the electric circuit boards 29 and the signal line 36 and thereafter displayed on the monitor 55.

As shown in FIG. 4 and FIG. 5, a distal end of an image pickup case 95 that covers a lens close to the image pickup device 27 configuring the lens unit 22, the image pickup device 27, the electric circuit boards 29, and the distal end side of the signal line 36 is fixed to the outer circumference 31g on a proximal end side of the distal end portion main body 31.

Note that a fixing position of the image pickup case 95 to the outer circumference 31g of the distal end portion main body 31 may be set forward relative to a position shown in FIG. 4 and FIG. 5. A male screw 45 with which the female screw 6 of the adapter 1 is screwed may be formed in an outer circumference of the image pickup case 95.

As shown in FIG. 4, FIG. 5, and FIG. 7 to FIG. 9, a lead wire 26 for distinguishing a type of the adapter 1 with a not-shown CPU in the apparatus main body 50 by, when the adapter 1 is mounted on the mounting and detaching section 40, energizing the identification resistor 3 via the terminals 34 and 35 and the pins 3p with electric power from a not-shown energizing unit provided in the apparatus main body 50 and transmitting a resistance value of the identification resistor 3 to a not-shown identification circuit in the apparatus main body 50 is inserted through the universal cord 17, the operation section 15, and the insertion section 10.

Note that, as in the past, in a configuration in which a distal end of the lead wire 26 is directly connected to the terminals 34 and 35, the distal end of the lead wire 26 has to be directly connected to the terminals 34 and 35 via a space in the mounting and detaching section 40, that is, a lead wire insert-through hole formed in the distal end portion main body 31. However, as explained above, the mounting and detaching section 40 is formed smaller in diameter than the other part 41. Therefore, it is difficult to separately secure the space for inserting the lead wire 26 in the mounting and detaching section 40.

Therefore, in the present embodiment, a configuration is adopted in which the distal end of the lead wire 26 is located behind the mounting and detaching section 40 and the distal end of the lead wire 26 and the terminals 34 and 35 are electrically connected by a flexible board 23 inserted at least through the mounting and detaching section 40 along the inserting direction S.

More specifically, as shown in FIG. 8 and FIG. 9, the flexible board 23 is configured from a semicircular terminal connecting section 23a to which proximal ends of the terminals 34 and 35 are electrically connected, a gap passing section 23b concatenated to the terminal connecting section 23a, a lens frame cutout passing section 23c concatenated to the gap passing section 23b, and a lead wire connecting section 23d concatenated to the lens frame cutout passing section 23c.

As shown in FIG. 8 and FIG. 9, the terminal connecting section 23a is formed to be bent approximately 90° to a right side in FIG. 8 and FIG. 9 from a distal end of the gap passing section 23b to thereby being located not to be superimposed on the lens units 21 and 22 with respect to the inserting direction S in front of the lens unit 22. Note that the terminal connecting unit 23a is formed in the semicircular shape in order to prevent the terminal connecting section 23a from blocking a light beam made incident on the lens unit 22 from the lens unit 21.

On a distal end face in a vicinity of an opening end portion 23ak of the semicircular terminal connecting section 23a, as shown in FIG. 4 and FIG. 5, the terminals 34 and 35 are electrically connected by solder or the like in a space 31*dh* in front of a distal end of the lens frame 32 in the recessed section 31*d*.

Note that the terminals 34 and 35 are electrically connected to the distal end face in the vicinity of the opening end portion 23*ak* of the semicircular terminal connecting section 23*a* in order to dispose the distal ends of the terminals 34 and 35 to be separated from each other to hold the objective lens 21*a* on the distal end face 31*ts* as explained above.

Therefore, if a shape of the terminal connecting section 23*a* is changed, an exposed position of the distal end on the distal end face 31*ts* of the terminals 34 and 35, the proximal ends of which are electrically connected to the terminal connecting section 23*a*, can be freely set.

Note that, since the flexible board 23 is used for the electric connection of the terminals 34 and 35, it is possible to freely set insert-through positions of the terminals 34 and 35 in the projecting section 31*t*. This is because it is difficult to form, with a lead wire, the semicircular terminal connecting section 23*a* in the present embodiment.

As shown in FIG. 4 and FIG. 6, in the mounting and detaching section 40, the gap passing section 23*b* is inserted through a gap 33 provided by forming a cutout 31*k* in the inner circumference 31*n* on left in FIG. 6 between an outer circumference 32*g* of the lens frame 32 and the inner circumference 31*n* formed by the recessed section 31*d*.

Note that the cutout 31*k* may be formed in the outer circumference 32*g* of the lens frame 32 or may be formed in both of the inner circumference 31*n* and the outer circumference 32*g*. The gap 33 may be provided by a groove formed in at least one of the inner circumference 31*n* and the outer circumference 32*g*, and is not limited to be provided by the cutout 31*k*.

Note that a forming position of the gap 33 by the cutout 31*k* is not limited to left in FIG. 6 and may be right or may be an upper or lower part.

If the forming position of the gap 33 changes, a passing position of the gap passing section 23*b* also changes. Therefore, a bending direction of the terminal connecting section 23*a* from the distal end of the gap passing section 23*b* also changes in order to locate the terminal connecting section 23*a* in front of the lens unit 22.

As shown in FIG. 4 and FIG. 7 to FIG. 9, in the other part 41, the lens frame cutout passing section 23*c* passes a cutout 32*k* formed on left in FIG. 7 to FIG. 9 in the outer circumference 32*g* of the lens frame 32 to thereby be located along left of the outer circumference 32*g* of the lens frame 32.

Note that a forming position of the cutout 32*k* is not limited to the left in FIG. 7 to FIG. 9 and may be right or may be an upper or lower part according to the forming position of the gap 33.

As shown in FIG. 4 and FIG. 7, in a position behind the mounting and detaching section 40, that is, in the other part 41, the lead wire connecting section 23*d* is a part to which the distal end of the lead wire 26 is electrically connected by solder or the like. The lead wire connecting section 23*d* is located along left of an outer circumference of the device frame 28. Note that, as explained above, a disposition position of the lead wire connecting section 23*d* with respect to the outer circumference of the device frame 28 is different according to a disposition position of the lens frame cutout passing section 23*c*.

As explained above, the terminals 34 and 35 and the distal end of the lead wire 26 are electrically connected via the flexible board 23.

In this way, in the present embodiment, the terminals 34 and 35 are shown as being electrically connected to the semicircular terminal connecting section 23*a* of the flexible board 23 in the space 31*dh* of the recessed section 31*d* in the mounting and detaching section 40.

The distal end of the lead wire 26 is electrically connected to the lead wire connecting section 23*d* of the flexible board in the other part 41 behind the mounting and detaching section 40.

Further, in the mounting and detaching section 40, the flexible board 23 is shown as being inserted through the gap 33 provided by forming the cutout 31*k* in the inner circumference 31*n* between the outer circumference 32*g* of the lens frame 32 and the inner circumference 31*n* formed by the recessed section 31*d*.

Consequently, the distal end of the lead wire 26 is electrically connected to the proximal end of the flexible board 23 in the other part 41. The distal end of the flexible board 23 is electrically connected to the terminals 34 and 35 in the mounting and detaching section 40. Therefore, the lead wire 26 is not inserted through the mounting and detaching section 40.

Therefore, since it is unnecessary to separately provide an insert-through space for the lead wire 26 in the mounting and detaching section 40, that is, in the distal end portion main body 31 as in the past, it is possible to reduce the mounting and detaching section 40 in diameter.

In the mounting and detaching section 40, the gap passing section 23*b* is inserted through the gap 33 because the cutout is formed in the inner circumference 31*n* between the outer circumference 32*g* and the inner circumference 31*n*, that is, the gap passing section 23*b* is inserted through the gap 33 formed using a fitting surface of the outer circumference 32*g* and the inner circumference 31*n*. Therefore, it is unnecessary to separately provide an insert-through space for the flexible board 23 in the distal end portion main body 31. Further, the distal end portion main body 31 is not increased in diameter according to the formation of the gap 33. Therefore, it is possible to reduce the mounting and detaching section 40 in diameter.

In the present embodiment, the terminals 34 and 35, the distal ends of which are exposed on the distal end face 31*ts*, used for distinguishing, when the adapter 1 is mounted on the mounting and detaching section 40, a type of the adapter 1 by energizing the identification resistor 3 via the pins 3*p* is shown as being provided to be separated from each other in the positions where the terminals 34 and 35 sandwich the objective lens 21*a* because the terminal connecting section 23*a* of the flexible board 23 is formed in the semicircular shape and the proximal ends of the terminals 34 and 35 are electrically connected to the vicinity of the opening end portion 23*ak*.

Consequently, in a region other than the disposition region of the objective lens 21*a* on the distal end face 31*ts*, it is possible to expose the distal ends of the terminals 34 and 35 without securing a large area of the distal end face 31*ts*. That is, since the projecting section 31*t*, through which the terminals 34 and 35 are inserted, is not increased in diameter, it is possible to reduce the mounting and detaching section 40 in diameter.

Since the terminal connecting section 23*a*, to which the terminals 34 and 35 are electrically connected, is a part of the flexible board 23, it is possible to change the shape of the terminal connecting section 23*a*. Further, since connecting positions of the terminals 34 and 35 to the terminal connecting section 23a can also be freely set, it is possible to freely set the insert-through positions of the terminals 34 and 35 in the projecting section 31t in positions where the projecting section 31t is not increased in diameter. Therefore, it is possible to reduce the mounting and detaching section 40 in diameter.

Further, since the terminals 34 and 35 are electrically connected to the terminal connecting section 23a located to be bent approximately 90° from the distal end of the gap passing section 23b, it is possible to further reduce the connecting section for the terminals in size than the configuration in which the lead wire is directly connected to the terminals. Therefore, it is possible to reduce the mounting and detaching section in diameter.

Consequently, it is possible to provide the endoscope 20 including a configuration that can realize a reduction in the diameter of the mounting and detaching section 40 even if the mounting and detaching section 40 includes a member for adapter identification.

(Second Embodiment)

Figure 10:
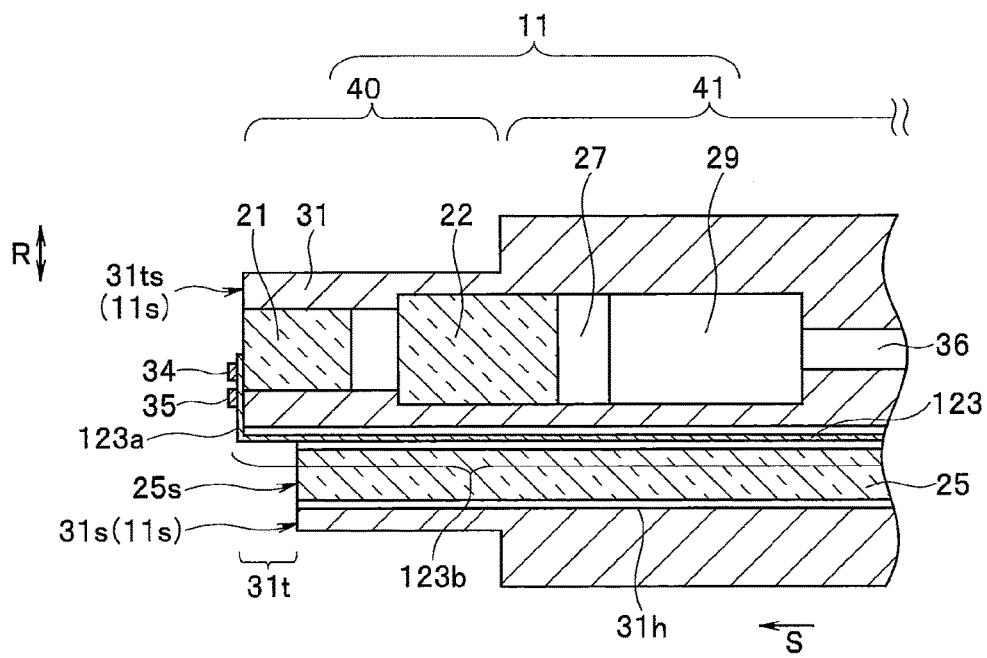
FIG. 10 is a partial sectional view schematically showing a part of a distal end portion of an insertion section of an endoscope in a second embodiment.
Figure 11:
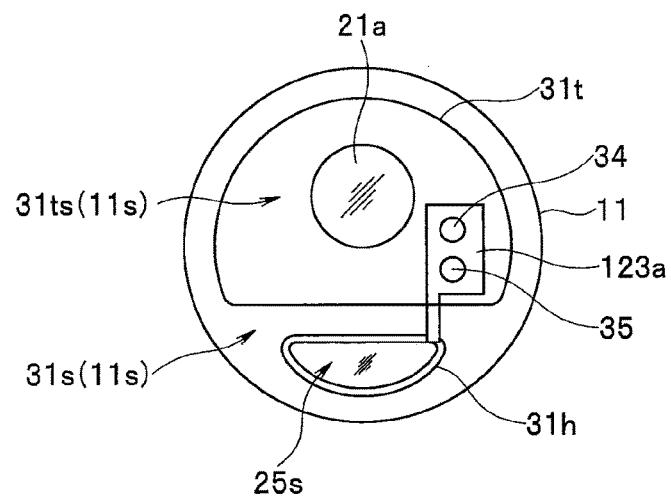
FIG. 11 is a plan view of a distal end face of the distal end portion in FIG. 10.
Figure 12:
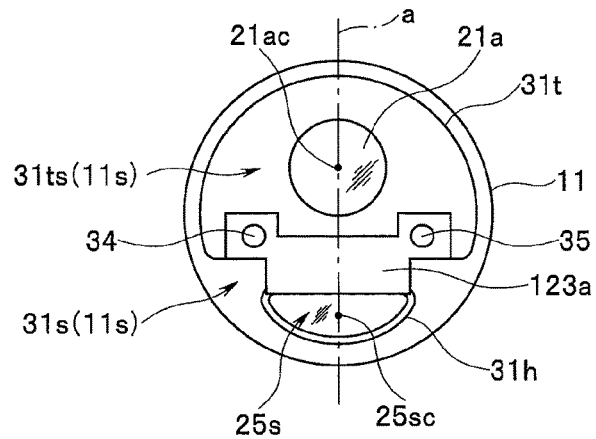
FIG. 12 is a plan view showing a modification of a disposition position of terminals on a distal end face of a projecting section in FIG. 10.

FIG. 10 is a partial sectional view schematically showing a part of a distal end portion of an insertion section of an endoscope in the present embodiment. FIG. 11 is a plan view of a distal end face of the distal end portion in FIG. 10. FIG. 12 is a plan view showing a modification of a disposition position of terminals on a distal end face of a projecting section in FIG. 10.

A configuration of the endoscope in the second embodiment is different from the endoscope in the first embodiment shown in FIG. 1 to FIG. 9 explained above in that, in a mounting and detaching section, a flexible board is inserted through a light guide holding hole. Therefore, only this difference is explained. Components same as the components in the first embodiment are denoted by the same reference numerals and signs and explanation of the components is omitted.

As shown in FIG. 10, in the present embodiment, a flexible board 123 that electrically connects the terminal 34 and 35 and distal end of the lead wire 26 is configured from a terminal connecting section 123a, a light guide holding hole insert-through section 123b concatenated to the terminal connecting section 123a, and a not-shown lead wire connecting section concatenated to the light guide holding hole insert-through section 123b.

The light guide holding hole insert-through section 123b is inserted through the light guide holding hole 31h together with the light guide 25. That is, in the mounting and detaching section 40, the light guide holding hole insert-through section 123b is inserted through the light guide holding hole 31h.

Note that, in FIG. 10, the light guide holding hole insert-through section 123b is inserted through the light guide holding hole 31h in the other part 41 as well. However, without being limited thereto, a part of the flexible board 123 inserted through the other part 41 may be drawn out to an outside of the light guide holding hole 31h.

In the present embodiment as well, although not shown in the figure, the light guide holding hole insert-through section 123b is drawn out to the outside of the light guide holding hole 31h in the other part 41. In a position behind the mounting and detaching section 40, the distal end of the lead wire 26 is electrically connected to a lead wire connecting section concatenated to the light guide holding hole insert-through section 123b.

Further, in the present embodiment, in front of the light guide holding hole 31h, the terminal connecting section 123a is bent approximately 90° from a distal end of the light guide holding hole insert-through section 123b and located to be opposed to the distal end face 31ts. As shown in FIG. 10 to FIG. 12, the terminal connecting section 123a is fixed to a position other than the disposition region of the objective lens 21a on the distal end face 31ts.

The terminals 34 and 35 are electrically connected to, by solder or the like, a distal end face of the terminal connecting section 123a fixed to the distal end face 31ts.

Note that, as in the first embodiment explained above, by changing a shape of the terminal connecting section 123a as shown in FIG. 11 and FIG. 12, connecting positions of the terminals 34 and 35 to the terminal connecting section 123a may be provided in positions shifted to an outer circumferential edge side of the distal end face 31ts from the positions where the terminals 34 and 35 sandwich the objective lens 21a as shown in FIG. 12. More specifically, the terminals 34 and 35 may be provided to be separated from each other in positions line-symmetrical with respect to the line "a". As shown in FIG. 11, the terminals 34 and 35 may be located side by side.

Note that, as explained above, in disposition positions of the terminals 34 and 35 in FIG. 12, the projecting section 31t can be further reduced in diameter than in disposition positions of the terminals 34 and 35 in FIG. 11.

Note that the other components are the same as the components in the first embodiment explained above.

In this way, in the present embodiment, in the flexible board 123, at least a part in the mounting and detaching section 40 is shown as being inserted through the light guide holding hole 31h.

Consequently, it is unnecessary to separately provide a space for inserting through the flexible board 123 in the mounting and detaching section 40, that is, in the distal end portion main body 31. Therefore, a configuration of the distal end portion main body 31 is simplified. Further, it is possible to reduce the mounting and detaching section 40 in diameter.

In the present embodiment, the connection of the terminals 34 and 35 to the flexible board 123 is shown as being performed to the terminal connecting section 123a fixed to the distal end face 31ts.

Consequently, the space 31dh for electrically connecting the terminals 34 and 35 to the flexible board 123 in the distal end portion main body 31 as in the first embodiment explained above is unnecessary. Therefore, it is possible to attain a reduction in a diameter of the mounting and detaching section 40.

Further, since the terminals 34 and 35 are electrically connected to the terminal connecting section 123a located to be bent approximately 90° from the distal end of the light guide holding hole insert-through section 123b, it is possible to further reduce the connecting section for the terminals in size than the configuration in which the lead wire is directly connected to the terminals. Therefore, it is possible to reduce the mounting and detaching section in diameter.

In the first embodiment explained above, water tightness has to be secured for three sections, i.e., the hole in which the lens unit 21 is provided, the light guide holding hole 31h, and the gap 33 in the distal end portion main body 31. On the other hand, in the present embodiment, water tightness only has to be secured for two sections, i.e., the hole in which the lens unit 21 is provided and the light guide holding hole 31h. Therefore, it is easy to secure water tightness for the mounting and detaching section 40. Further, assemblability is also improved.

Further, simply by changing a shape of the terminal connecting section 123a and changing the connecting positions of the terminals 34 and 35 to the terminal connecting section 123a, it is possible to freely change the connecting positions of the terminals 34 and 35 on the distal end face 31ts.

Note that other effects are the same as the effects in the first embodiment explained above.

(Third Embodiment)

Figure 13:
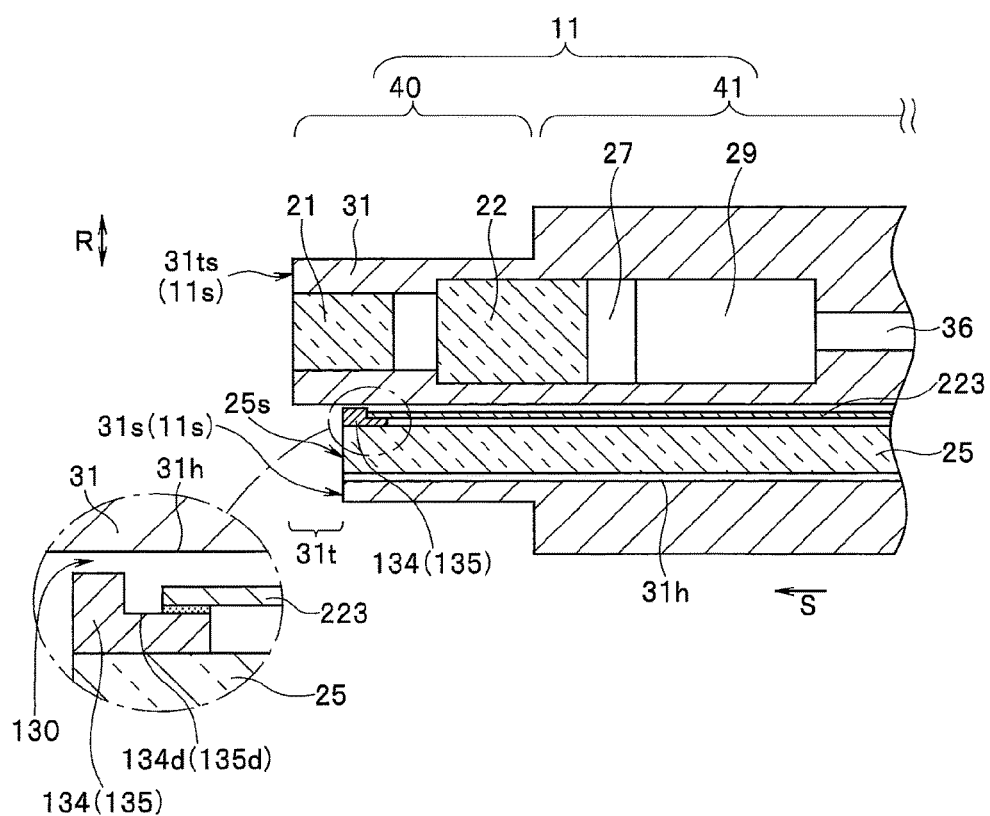
FIG. 13 is a partial sectional view schematically showing a part of a distal end portion of an insertion section of an endoscope in a third embodiment.
Figure 14:
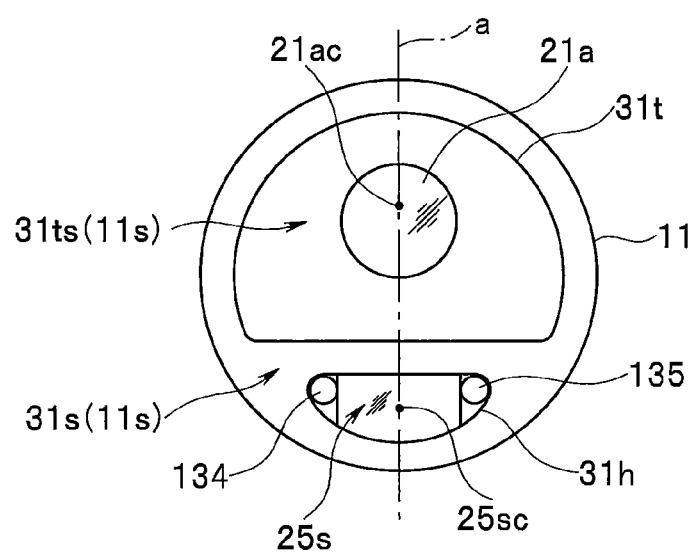
FIG. 14 is a plan view of a distal end face of the distal end portion in FIG. 13.

FIG. 13 is a partial sectional view schematically showing a part of a distal end portion of an insertion section of an endoscope in the present embodiment. FIG. 14 is a plan view of a distal end face of the distal end portion in FIG. 13.

A configuration of the endoscope in the third embodiment is different from the endoscope in the second embodiment shown in FIG. 10 to FIG. 12 explained above in that terminals are also provided in a light guide holding hole. Therefore, only this difference is explained. Components same as the components in the second embodiment are denoted by the same reference numerals and signs and explanation of the components is omitted.

As shown in FIG. 13 and FIG. 14, in the present embodiment as well, a flexible board 223 is inserted through the light guide holding hole 31h. Therefore, a part of the flexible board 223 located in the mounting and detaching section 40 is also naturally inserted through the light guide holding hole 31h.

As in the second embodiment explained above, a proximal end side of the flexible board 223 is drawn out to the outside of the light guide holding hole 31h in the other part 41. The distal end of the lead wire 26 is electrically connected to a not-shown lead wire connecting section provided at the proximal end of the flexible board 223.

In the present embodiment, in the distal end in the light guide holding hole 31h, terminals 134 and 135 are provided such that distal ends of the terminals 134 and 135 are exposed on the distal end face 31s together with the emission end face 25s of the light guide 25 from a distal end opening as shown in FIG. 14. Note that functions of the terminals 134 and 135 are the same as the functions of the terminals 34 and 35 explained above.

As shown in FIG. 14, in the light guide holding hole 31h, as in the first and second embodiments explained above, the terminals 134 and 135 are provided to be separated from each other in positions shifted to an outer circumferential edge of the distal end face 31s from the positions where the terminals 134 and 135 sandwich the objective lens 21a on the distal end face 31s. More specifically, the terminals 134 and 135 are provided to be separated from each other in positions line-symmetrical with respect to the line "a".

Further, in the light guide holding hole 31h, the terminals 134 and 135 are provided to be separated from each other in positions between an inner circumferential face of the light guide holding hole 31h and an outer circumferential face of the light guide 25.

As shown in an enlarged view of FIG. 13, a part of the terminals 134 and 135 are set in contact with the outer circumferential face of the light guide 25 having insulation. Parts of the terminals 134 and 135 on an opposite side of contact parts with the light guide 25 are located to be separated to have a gap 130 with respect to the distal end portion main body 31.

Further, in the present embodiment, a distal end side of the flexible board 223 is divided into two, though not shown. The respective distal ends are electrically connected respectively to step sections 134d and 135d formed in the terminals 134 and 135 respectively, by solder or the like, in the light guide holding hole 31h, at positions lower than an opposing surface of the terminals 134 and 135, opposing to the distal end portion main body 31.

With such a configuration, a part of the terminals 134 and 135 are in contact with the light guide 25 having insulation. The gap 130 is formed between the terminals 134 and 135 and the distal end portion main body 31. Further, a connecting section on the distal end side of the flexible board 223 to the terminals 134 and 135 is electrically connected to the positions lower than the opposing surface to the distal end portion main body 31 in the terminals 134 and 135. Therefore, unlike the first and second embodiments explained above, even if the insulating members 88 are not coated around the terminals 134 and 135, the terminals 134 and 135 are prevented from coming into contact with the distal end portion main body 31 to be short-circuited.

Note that other components are the same as the components in the second embodiment explained above.

In this way, in the present embodiment, the terminals 134 and 135 are shown as being provided such that the distal ends are exposed on the distal end face 31 s in the light guide holding hole 31h. The distal end of the flexible board 223 is shown as being electrically connected to the terminals 134 and 135 in the light guide holding hole 31h.

Consequently, it is unnecessary to dispose the terminals on the distal end face 31ts as in the second embodiment explained above. Therefore, since the projecting section 31t can be reduced in diameter by the size of the terminals, it is possible to reduce the mounting and detaching section 40 in diameter. Note that other effects are the same as the effects in the second embodiment explained above.

In the first to third embodiments explained above, the endoscope for industrial use is explained as an example. However, it goes without saying that the present invention may be applied to an endoscope for medical use.

What is claimed is:

1. An endoscope in which two or more kinds of adapters are individually detachably attachable to a distal end portion located at a distal end in an inserting direction of an insertion section, the endoscope comprising:

a mounting and detaching section located on the distal end side in the inserting direction in the distal end portion, a connecting section of the adapter being detachably mountable on an outer circumference of the mounting and detaching section and a diameter of the mounting and detaching section being smaller than a diameter of another part of the distal end portion;

a terminal provided to be exposed on a distal end face of the distal end in the inserting direction in the distal end portion in the mounting and detaching section, when the adapter is mounted on the outer circumference of the mounting and detaching section, the terminal coming into contact with an identification resistor provided in the adapter and having different resistance values for each of the adapters;

a lead wire inserted through the insertion section, the lead wire energizing the identification resistor via the terminal;

a flexible board inserted through at least the mounting and detaching section, the flexible board being electrically connected to the terminal in the mounting and detaching section and electrically connected to a distal end in the inserting direction of the lead wire in a position behind the mounting and detaching section in the inserting direction;

an objective lens exposed on the distal end face;

a light guide exposed on the distal end face, the light guide configured to supply illumination light to the adapters,
wherein the terminal comprises an anode terminal and a cathode terminal, and when a straight line connecting the anode terminal and the cathode terminal is considered as a border in a plan view of the distal end face, the objective lens is provided so that a center of the objective lens is arranged on a first side of the distal end face with respect to the straight line and the light guide is provided so that a center of the light guide is arranged on a second side, the second side opposite of the straight line as compared to the first side.

2. The endoscope according to claim 1, further comprising:
   a first frame provided in the distal end portion, the first frame holding a first objective optical system; and
   a second frame provided in the distal end portion, the second frame holding a second objective optical system located behind the first objective optical system in the inserting direction and a part of an outer circumference of the second frame being fixed to an inner circumference of the first frame, wherein
   in the mounting and detaching section, the terminal and a distal end in the inserting direction of the flexible board are electrically connected and the flexible board is inserted through a gap between the outer circumference of the second frame and the inner circumference of the first frame.

3. The endoscope according to claim 2, wherein the gap comprises at least one of a cutout formed on the outer circumferential face of the second frame inwardly toward an inner circumference of the second frame and a cutout formed on the inner circumferential face of the first frame outwardly toward an outer circumference of the first frame.

4. The endoscope according to claim 2, wherein the gap comprises at least one of a cutout formed on an outer circumferential face of the second frame inwardly toward an inner circumference of the second frame with respect to a position where the first frame and the second frame are fitted and fixed to each other, and a cutout formed on an inner circumferential face of the first frame outwardly toward an outer circumference of the first frame with respect to the position where the first frame and the second frame are fitted and fixed to each other.

5. The endoscope according to claim 2, wherein the flexible board comprises a gap passing section that passes the gap, and a terminal connecting section connected to a distal end side of the gap passing section in the inserting direction and electrically connected to the terminal.

6. The endoscope according to claim 5, wherein the terminal connecting section is bent from a distal end of the gap passing section toward the inner circumference of the first frame, and formed in a semicircular shape.

7. The endoscope according to claim 2, wherein a cutout through which the flexible board passes is formed on an outer circumferential face of the second frame on a proximal side with respect to a position where the first frame and the second frame and fitted and fixed to each other.

8. The endoscope according to claim 1, further comprising a first frame provided in the distal end portion, the first frame holding a first objective optical system and holding a light guide for supplying illumination light to the adapter, wherein
   in the mounting and detaching section, the flexible board is inserted through a light guide holding hole formed in the first frame and through which the light guide is inserted along the inserting direction.

9. The endoscope according to claim 8, wherein
   a distal end side in the inserting direction of the flexible board is fixed to the distal end face of the distal end portion by being bent in front of the light guide holding hole in the inserting direction, and
   the terminal is electrically connected to a part of the flexible board fixed to the distal end face.

10. The endoscope according to claim 8, wherein
    the terminal is provided in the light guide holding hole in the mounting and detaching section, and
    in the light guide holding hole, the terminal and a distal end in the inserting direction of the flexible board are electrically connected.

11. The endoscope according to according to claim 1, wherein the terminal is configured from an anode terminal electrically connected to an anode side of the identification resistor and a cathode terminal electrically connected to a cathode side of the identification resistor.

12. The endoscope according to according to claim 1, wherein the flexible board is an arc shape that is configured to extend about a portion of an outer circumferential edge of the objective lens on the first side.

13. The endoscope according to according to claim 1, wherein a portion of the straight line overlaps a portion of the objective lens in the plan view of the distal end face.

* * * * *